United States Patent
De Bruyker et al.

(10) Patent No.: US 8,617,899 B2
(45) Date of Patent: Dec. 31, 2013

(54) ENHANCED DROP MIXING USING MAGNETIC ACTUATION

(75) Inventors: Dirk De Bruyker, Palo Alto, CA (US); Ali Asgar Saleem Bhagat, Cincinnati, OH (US); Alan G. Bell, Mountain View, CA (US); Michael I. Recht, Mountain View, CA (US); Francisco E. Torres, San Jose, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 1256 days.

(21) Appl. No.: 12/031,519

(22) Filed: Feb. 14, 2008

(65) Prior Publication Data
US 2011/0263464 A1 Oct. 27, 2011

(51) Int. Cl.
| G01N 25/20 | (2006.01) |
| G01N 27/00 | (2006.01) |
| G01N 25/00 | (2006.01) |
| C12M 1/02  | (2006.01) |

(52) U.S. Cl.
USPC ........... 436/147; 436/174; 436/180; 436/149; 436/150; 436/809; 422/82.12; 422/68.1; 422/503; 422/504; 422/224; 422/225; 435/302.1

(58) Field of Classification Search
USPC ......... 436/174, 180, 806, 149–151, 147, 526; 422/500, 503–504, 224–225, 82.12, 422/63–68.1; 366/273–274; 435/302.1
See application file for complete search history.

(56) References Cited

U.S. PATENT DOCUMENTS

| 3,650,698 A * | 3/1972 | Adler ............................. 422/73 |
| 3,752,443 A | 8/1973 | Lichtenstein |

(Continued)

FOREIGN PATENT DOCUMENTS

WO    2007101174 A2    9/2007

OTHER PUBLICATIONS

Shikida, M. et al., "Magnetic handling of Droplet in Micro Chemical Analysis System Utilizing Surface Tension and Wettability," Micro Electro Mechanical Systems, 2004; 17th IEEE Int'l Conf. on (MEMS), Maastricht, Netherlands, Jan. 25-29, 2004, Piscataway, NJ, US, IEEE, US Jan. 25, 2004, pp. 359-362.

(Continued)

Primary Examiner — Brian R Gordon
(74) Attorney, Agent, or Firm — Fay Sharpe LLP

(57) ABSTRACT

A method and device for merging and mixing at least two separate and distinct fluid drops on a substrate, includes a drop merging area on the surface, where a first magnetic material is placed at a first location. A first drop of fluid is then placed at the first location on the surface, resulting in the first magnetic material being at least partially positioned within the first drop of fluid. A second drop of fluid is then placed at a second location on the surface of the drop merging area. A magnetic field is applied by a varying magnetic field generator to at least a portion of the drop merge area of the substrate, which includes at least the first location on the substrate. The varying magnetic field will act on the first magnetic material to move the first magnetic material within the first drop of fluid, causing a stirring of the fluid. A drop merging force from a drop merging mechanism is applied to at least one of the first drop of fluid and the second drop of fluid within the drop merge area. This causes at least one of the first drop of fluid and the second drop of fluid to move toward the other and make contact. The internal stirring of the fluid in the first drop of fluid by the movement of the magnetic material enhances the mixing of the constituents of the first drop of fluid and the constituents of the second drop of fluid.

12 Claims, 19 Drawing Sheets

(56) References Cited

U.S. PATENT DOCUMENTS

| | | | |
|---|---|---|---|
| 3,995,835 | A | 12/1976 | Cichy et al. |
| 4,018,886 | A * | 4/1977 | Giaever .................... 436/526 |
| 4,310,253 | A * | 1/1982 | Sada et al. .................. 366/273 |
| 6,147,763 | A | 11/2000 | Steinlechner |
| 7,141,210 | B2 | 11/2006 | Bell et al. |
| 7,147,763 | B2 | 12/2006 | Elrod et al. |
| 7,189,259 | B2 * | 3/2007 | Simionescu et al. ......... 623/2.42 |
| 7,454,988 | B2 * | 11/2008 | Tan .......................... 73/863.21 |
| 8,007,739 | B2 * | 8/2011 | Pollack et al. ................ 422/509 |
| 8,088,578 | B2 * | 1/2012 | Hua et al. ..................... 435/6.1 |
| 8,093,064 | B2 * | 1/2012 | Shah et al. ................... 436/150 |
| 8,189,186 | B2 * | 5/2012 | Beer ............................. 356/244 |
| 8,216,855 | B2 * | 7/2012 | Pipper et al. ................. 436/526 |
| 8,389,297 | B2 * | 3/2013 | Pamula et al. ............... 436/526 |
| 8,440,150 | B2 * | 5/2013 | Den Dulk et al. ............ 422/537 |
| 8,470,606 | B2 * | 6/2013 | Srinivasan et al. ........... 436/180 |
| 2003/0183525 | A1 | 10/2003 | Elrod et al. |
| 2005/0036908 | A1 * | 2/2005 | Yu et al. ........................ 422/58 |
| 2005/0135455 | A1 * | 6/2005 | Peeters et al. .................. 374/31 |
| 2006/0078999 | A1 | 4/2006 | Bell et al. |
| 2006/0132542 | A1 | 6/2006 | De Bruyker et al. |
| 2006/0186048 | A1 * | 8/2006 | Tan .............................. 210/656 |
| 2007/0207272 | A1 | 9/2007 | Puri et al. |
| 2007/0243634 | A1 * | 10/2007 | Pamula et al. ............... 436/518 |
| 2007/0275415 | A1 * | 11/2007 | Srinivasan et al. ............ 435/7.4 |
| 2008/0226500 | A1 * | 9/2008 | Shikida et al. ............... 422/68.1 |
| 2009/0291433 | A1 * | 11/2009 | Pollack et al. .................... 435/6 |
| 2010/0068764 | A1 * | 3/2010 | Sista et al. ..................... 435/79 |
| 2010/0258441 | A1 * | 10/2010 | Sista et al. ................... 204/451 |
| 2010/0279374 | A1 * | 11/2010 | Sista et al. .................. 435/173.9 |
| 2011/0100823 | A1 * | 5/2011 | Pollack et al. ............... 204/601 |

OTHER PUBLICATIONS

Lehmann et al., "On-Chip Antibody Handling and Colorimetric Detection in a Magnetic Droplet Manipulation System", Microelectronic Engineering, Elsevier Publ. BV., Amsterdam, NL, vol. 84, No. 5-8, May 6, 2007, pp. 1669-1672.

EP Search Report, European Patent Application No. 091542403.3-1253, Dated Jul. 8, 2009, The Hague.

Lu, "A Magnetic Microstirrer and Array for Microfluidic Mixing", *Journal of Microelectromechanical Systems*, vol. 11, No. 5, Oct. 2002, pp. 462-469.

Hessel et al., "Micromixers-a review on passive and active mixing principles", *Chemical Engineering Science*, 60, 2005, pp. 2479-2501.

Agarwal et al., "Magnetically Driven Mixing within a Microarray Geometry using Functionalized Magnetic Nanoparticles", The $80^{th}$ ACS Colloid and Surface Science Symposium, Jun. 18-21, 2006.

Suzuki, et al., "A Magnetic Force Driven Chaotic Micro-Mixer", Proceedings Int. Conf. MEMS '02, 2002, Las Vegas, NV, pp. 40-43.

Mao, et al., "Overcoming The Diffusion Barrier: Ultra-Fast Micro-Scale Mixing Via Ferrofluids", Proceedings IEEE Transducers '07, 2007, Lyon, France, pp. 1829-1832.

Blummel, et al., "Protein repellent properties of covalently attached PEG coatings on nanostructured SiO2-based interfaces", *Biomaterials*, 2007, 28, pp. 4739-4747.

Jo, Seongbong, et al., "Surface modification using silanated poly(ethylene glycol)s", *Biomaterials*, vol. 21, Issue 6, Mar. 2000, pp. 605-616.

Ryu, et al., "Micro Magnetic Stir-Bars Integrated in Parylene surface-Micromachined Channels for Mixing and Pumping", $7^{th}$ International Conference on Miniaturized Chemical and Biochemical Analysis Systems, Squaw Valley, CA, Oct. 5-9, 2003.

* cited by examiner

ENHANCED DROP MIXING USING MAGNETIC ACTUATION

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided by the terms of Contract No. 1 R01 GM077435-01 awarded by National Institute of Health (NIH).

BACKGROUND

This application relates to the merging and mixing of individual drops of fluid, both in small numbers and in arrays. More specifically, the application provides apparatuses, methods and systems for placing drops on a surface and moving, merging and mixing the drops of fluid across the surface through use of electrostatic actuation, magnetic actuation or other mechanisms.

Mixing of fluid by use of magnetic mixers is a known process. Research in this area has included the use of MEMS technology to demonstrate enhanced micro-scale mixing (see, Lu, Ryu and Liu in Journal of Microelectromechanical Systems, Vol. 11, No. 5, October 2002, pp. 462-469; "Micromixers—a review on passive and active mixing principles" by V. Hessel et al, Chemical Engineering Science 60 (2005), pp. 2479-2501).

Additionally, research related to the use of magnetic particles and external fields to enhance mixing of biological reagents has been reported (see, "Magnetically Driven Mixing within a Microarray Geometry using Functionalized Magnetic Nanoparticles", by S. Agarwal and P. Laibinis, The 80th ACS Colloid and Surface Science Symposium (Jun. 18-21, 2006); "A Magnetic Force Driven Chaotic Micro-Mixer", by H. Suzuki and C. Ho, Proceedings Int. Conf. MEMS '02. (2002), Las Vegas, USA, pp. 40-43; and "Overcoming the Diffusion Barrier: Ultra-fast Micro-scale Mixing via Ferrofluids", by L. Mao and H. Koser, Proceedings IEEE Transducers '07 (2007), Lyon, France, pp. 1829-1832).

Another example of using magnetic particles to enhance mixing in moving fluids has been described in U.S. Pat. No. 3,995,835, titled, Magnetic mixer.

However, the literature has not revealed an apparatus, method or system appropriate for the uses addressed in this application.

INCORPORATION BY REFERENCE

The following patents, applications and articles, the disclosures of each being totally incorporated herein by reference are mentioned: U.S. Pat. No. 7,147,763, issued Dec. 12, 2006, entitled "Apparatus And Method For Using Electrostatic Force To Cause Fluid Movement", to Elrod et al.; U.S. Publication No. 2006/0132542A1, published Jun. 22, 2006, entitled "Apparatus And Method For Improved Electrostatic Drop Merging And Mixing", to De Bruyker et al.; U.S. Publication No. 2006/0078999A1, published Apr. 13, 2006, entitled "Apparatus And Method For A Nanocalorimeter For Detecting Chemical Reactions", to Bell et al.; U.S. Pat. No. 7,141,210, issued Nov. 28, 2006, to Bell et al., and by J. Blummel, N. Perschmann, D. Aydin, J. Drinjakovic, T. Surrey, M. Lopez-Garcia, H. Kessler, J. Spatz, "Protein repellent properties of covalently attached PEG coatings on nanostructured SiO2-based interfaces", Biomaterials (2007) 28, pp. 4739-4747., incorporated herein in its entirety.

BRIEF DESCRIPTION

A method and device for merging and mixing at least two separate and distinct fluid drops on a substrate, includes a drop merging area on the surface, where a first magnetic material is placed at a first location. A first drop of fluid is then placed at the first location on the surface, resulting in the first magnetic material being at least partially positioned within the first drop of fluid. A second drop of fluid is then placed at a second location on the surface of the drop merging area. A magnetic field is applied by a varying magnetic field generator to at least a portion of the drop merge area of the substrate, which includes at least the first location on the substrate. The varying magnetic field will act on the first magnetic material to move the first magnetic material within the first drop of fluid, causing a stirring of the fluid. A drop merging force from a drop merging mechanism is applied to at least one of the first drop of fluid and the second drop of fluid within the drop merge area. This causes at least one of the first drop of fluid and the second drop of fluid to move toward the other and make contact. The internal stirring of the fluid in the combined drop by the movement of the magnetic material enhances the mixing of the constituents of the first drop of fluid and the constituents of the second drop of fluid.

DETAILED DESCRIPTION

Figure 1A:
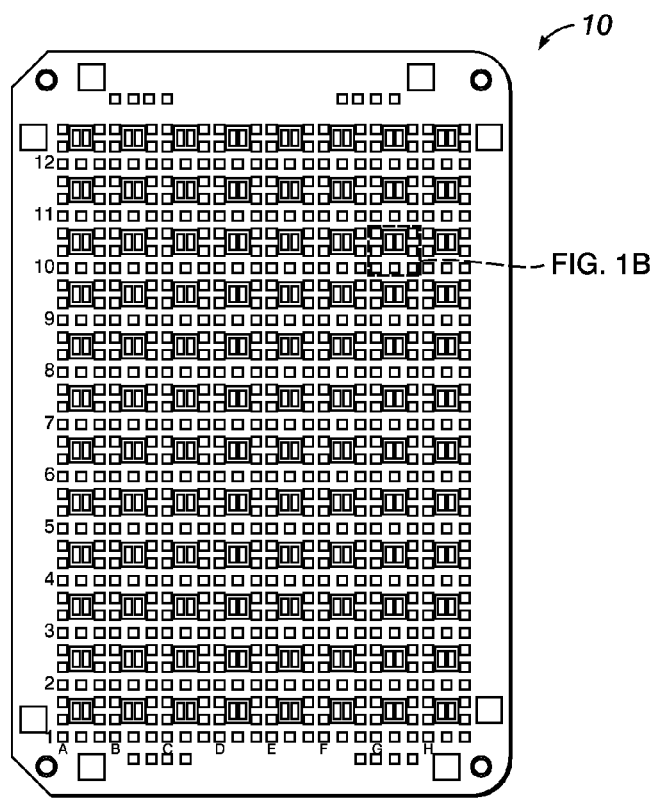
FIG. 1A illustrates an enthalpy array to which the concepts of the present application may be applied.

Turning to FIG. 1A, illustrated is an example of an enthalpy array 10 having a plurality of nanocalorimeter detector cells 12 which enable efficient biological research and drug discovery through direct measurement of molecular interaction. Such arrays can be fabricated using microfabrication technology in a 96-detector format and interface with automated laboratory equipment.

Figure 1B:
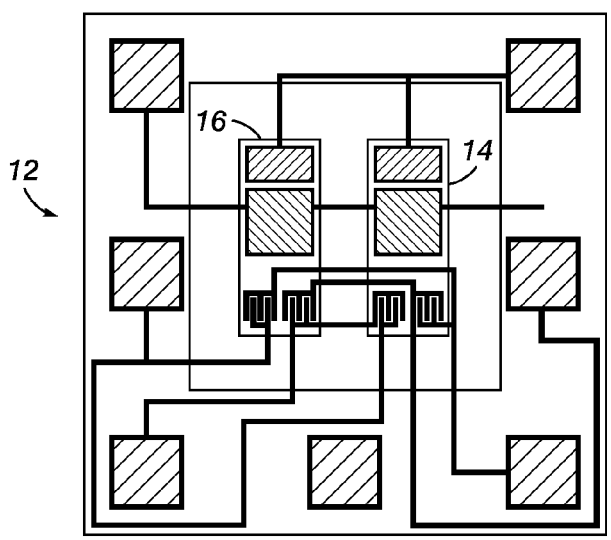
FIG. 1B depicts a detector cell of the enthalpy array of FIG. 1A.

As expanded on in FIG. 1B, each detector 12 consists of two identical adjacent sensing regions 14, 16 that provide a differential temperature measurement—one for a sample and one for a reference specimen. Each region is equipped with two thermistors, the four thermistors are combined in an interconnected Wheatstone bridge, and each region also has its own isothermal merging and mixing mechanism that is electrostatically driven. The thermistors may be made from vanadium oxide, amorphous silicon, or other appropriate material. In this description isothermal refers to the fact that the amount of heat generated inside the drops by the mixing and/or merging of the first drop of fluid and the second drop of fluid is small and may be below that which is capable of being detected by existing temperature detectors. The generated heat has been estimated by physical modeling, and is calculated to be in the 1 to 10 micro-Kelvin range. In today's typical temperature detectors, temperature differences of 30 micro-Kelvins or more are needed for detection. Therefore the mixing/merging temperature cannot be measured by existing nanocalorimeter detectors while, however, the reaction temperatures are detected by the nanocalorimeter detectors.

After the merging of two small (e.g., approximately 250 nl) drops, the detector measures the temperature change in the sample region 16 relative to a simultaneous merging of similar but non-reacting materials in the adjacent region 14. (As 16 and 14 are identical, one could also choose 14 as the sample region and 16 as the reference region.) This relative measurement effectively subtracts out correlated background drifts in temperature and other factors. When the temperature relative to the reference detector of the cell changes, the voltage output of the bridge changes proportionally.

Figure 2A:
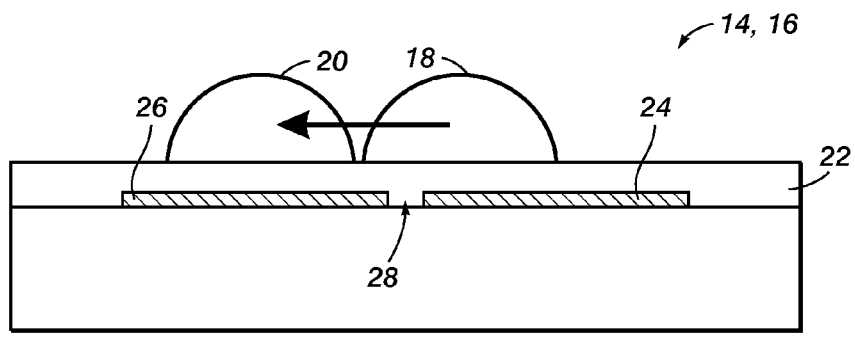
FIGS. 2A-2C show top and side versions of the merging of two separate independent droplets into a single droplet according to the concepts of FIGS. 1A and 1B.
Figure 2B:
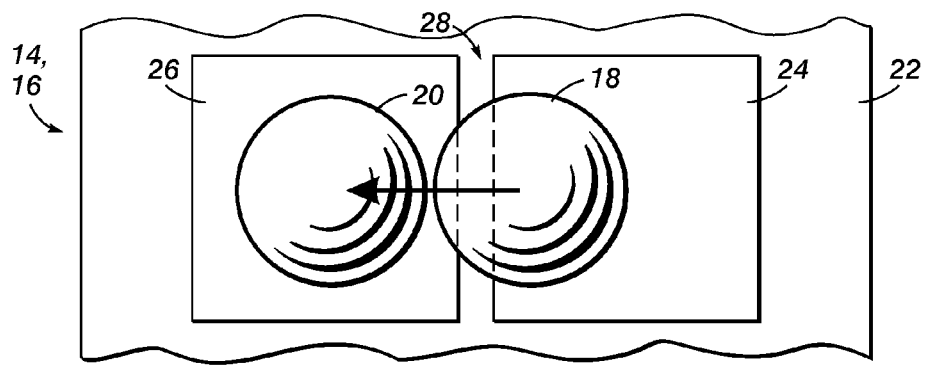
Figure 2C:
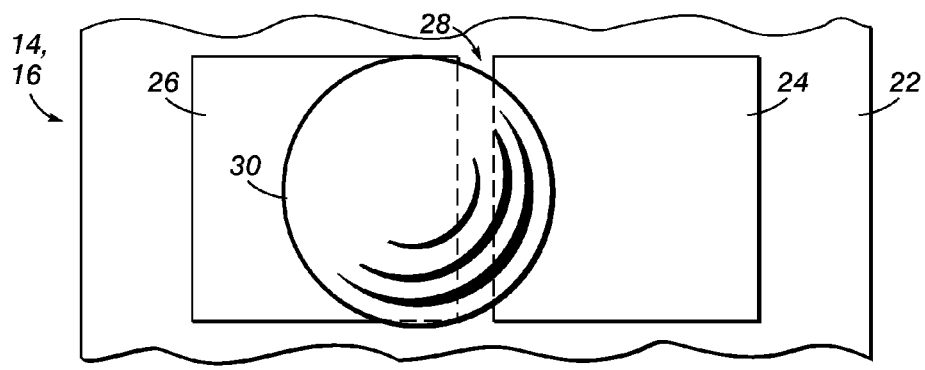

Referring now to FIGS. 2A-2C, illustrated is an example of the operation of a detector (14 or 16), where drops 18 and 20 are merged on surface 22 over electrodes 24 and 26. For drop merging, a first drop 18 is placed asymmetrically across gap 28 between electrodes 24 and 26, and a second drop 20 is placed in close proximity to the first drop, but on the opposite side of gap 28. For example, for 1 mm diameter droplets and a 50 µm electrode gap, the spacing between the droplets may range from approximately 50 µm to approximately 100 µm. When a voltage pulse is applied to the pair of electrodes 24 and 26 underneath the drops, e.g. 180V for 10-50 msec, due to electrostatic force drop 18 moves towards a centering position, touching and merging/mixing with drop 20 to form drop 30. In this configuration, the voltage required across electrodes 24 and 26 may range from a low of approximately 25V to approximately 100V when the droplets are spaced approximately 50 µm apart. With wider drop spacing, for example 250 µm or greater, a voltage exceeding 100V may be required.

Of course, nanocalorimeter detector 12 and regions 14, 16 may be configured in different parameter sizes and therefore the foregoing are provided only as examples. In some embodiments, a practical range of drop size for nanocalorimetry is in the hundreds of nanoliter (currently a preferred volume for a drop is 250 nanoliters) to the microliter range (1-50 microliter maximum). Additionally, while gap 28 is shown in these embodiments as a straight line gap, it is to be appreciated the gap may be defined by other than the straight line shown in FIGS. 2A-2C. Particularly, in some embodiments, an angled configuration has been used, such as shown in U.S. Pat. No. 7,147,763 B2 to Elrod et al, entitled, "Apparatus and Method for Using Electrostatic Force to Cause Fluid Movement", incorporated herein in its entirety.

The above electrostatic mixing/merging has been described in more detail in various patent applications of the assignee such as U.S. Pat. No. 6,147,763, entitled "Apparatus And Method For Using Electrostatic Force To Cause Fluid Movement", to Elrod et al., incorporated herein in its entirety.

In devices such as shown in FIGS. 1A, 1B, and 2, faster drop mixing acts to increase the sensitivity of the detector and enable a broader range of measurements. With faster mixing, reagents in the first and second drop come into close proximity of each other faster and a given reaction will result in a higher temperature peak sensed by the detector as there is less time for the reaction heat to dissipate. This allows smaller signals to be resolved than in the case of slower mixing. The increased mixing speed also makes it possible to measure reaction kinetics more readily. Therefore, methods and/or devices which increase the speed at which individual drops of fluid are merged and mixed would be considered useful.

It is to be appreciated of course arrays which may take advantage of the following concepts may be designed in other configurations and with different numbers and types of detectors. Also, faster mixing/merging of drops of fluid will be useful in areas other than enthalpy arrays. Therefore, while the following discusses methods and devices which increase the speed of such mixing/merging with particular attention to nanocalorimeter detectors and enthalpy arrays comprised of such detectors, it is understood such concepts may be applied in other areas with other devices and methods which would benefit from the disclosed concepts.

Upon merging, the constituents of the two drops (e.g. biomolecules) mix primarily through diffusion if there is no applied mixing, with an enhancing effect due to the momentum the moving drop possesses just prior to merging (The moving drop can be thought to be 'injected' into the stationary one. In some systems both drops may be made to move).

The time constant of purely diffusive mixing can be estimated by:

$$\tau_D = \frac{L^2}{D}$$

with L representing a characteristic length, and D the diffusion coefficient of the constituent molecules. This time constant can be calculated to be in the order of 800 seconds for nanocalorimeter type sizes/measurements wherein there is no enhancement of mixing by any means (e.g., (400 um)^2/2e-6 cm^2/sec=800 sec).

Fluorescent Resonant Energy Transfer (FRET) experiments, using solutions of fluorescently labeled DNA oligonucleotides as constituents and mimicking nanocalorimeter sizes/measurements, show 20-50 second time constants for mixing. The difference between this number and pure diffusive mixing can be attributed to the effect of the momentum of the moving drop.

Faster mixing, preferably with time constants less than the thermal dissipation time constant (i.e., 2-3 seconds) is desired, as it will increase sensitivity of the device and therefore improve its results and expand its areas of use.

Turning now to magnetic mixing, to increase mixing speed of the reagents in the drops, the present application teaches a concept of locating magnetic material in one or both of the drops to be mixed/merged (e.g., the reagent drops) and to apply a varying magnetic field to a drop merge area of the device during the mixing/merging operation to cause an internal disturbance in the drop(s). The merging itself is either achieved by applying a voltage to electrodes on the detector underneath the drops, as is the current practice, or to use the motion of the magnetic material to trigger the mixing/merging process.

One embodiment where the motion of the magnetic material is used to trigger the merging process employs a two stage magnetic actuation process. A first, strong magnetic field is applied during a short time, causing the drops to move toward one another for merging. Then, a second, weaker magnetic field is applied to increase the mixing speed of the reagents in the merged drop, while keeping the merged drop stationary. The specific values of the magnetic fields and the rate at which they are applied will vary in accordance with the particular application. Employing this embodiment means electrostatic actuation generated by voltage applied to electrodes on the detector underneath the drops is not required.

Placement of the magnetic material in a drop, and then supplying varying magnetic fields by use of, for example, a closely positioned magnet, results in forces being exerted on the magnetic materials by the varying magnetic field. As a result, the magnetic material inside the drop moves or spins around and the mixing of the two volumes of fluid is enhanced due to the stirring action internal to the drop. In this discussion, a drop of fluid is understood to mean a small volume of liquid in contact with a solid surface, that has both a solid-liquid interface as well as a liquid-gas or liquid-liquid interface. Thus, the drops in one embodiment will be positioned on a surface such as a substrate and will be in contact with air or other gas, i.e., the liquid-gas interface. In other embodiments, the drops may be positioned on a surface such as a substrate and also be immersed in another liquid. For instance, aqueous drops may be on a surface that is entirely immersed in oil, or some other liquid to which the liquid in the drop is immiscible. In an alternative embodiment, the aqueous drop will have a thin liquid film/coating of oil on its entire surface. Thus, the following descriptions are understood to incorporate and be applicable to these scenarios.

Figure 3A:
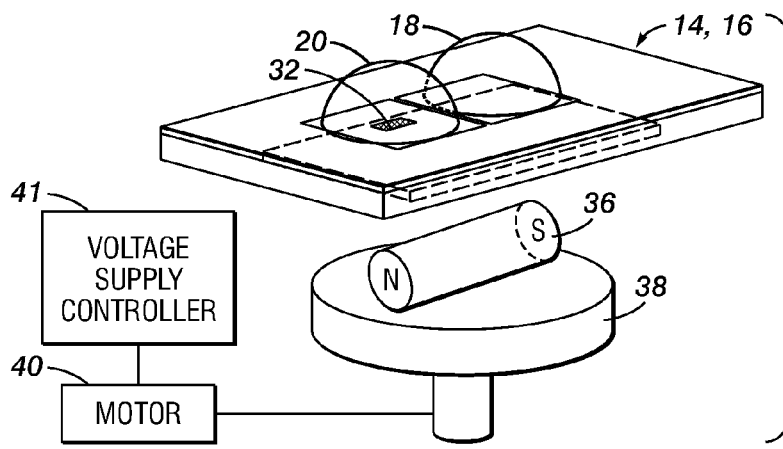
FIGS. 3A-3C show magnetic mixing using a microscale bar stirring technique according to the concepts of the present application.
Figure 3B:
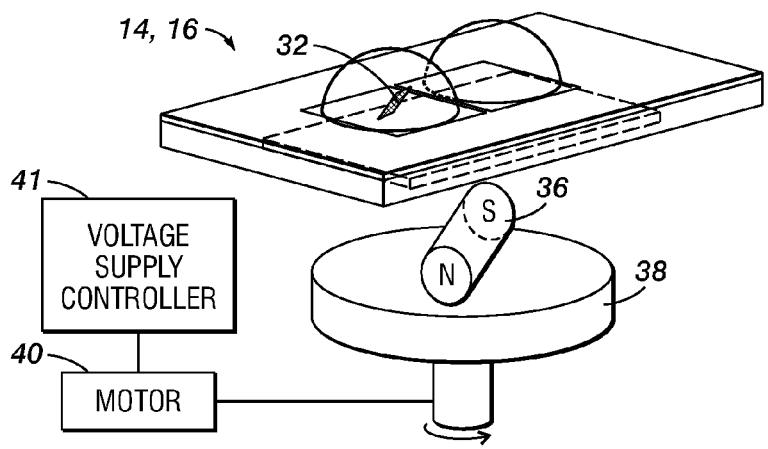
Figure 3C:
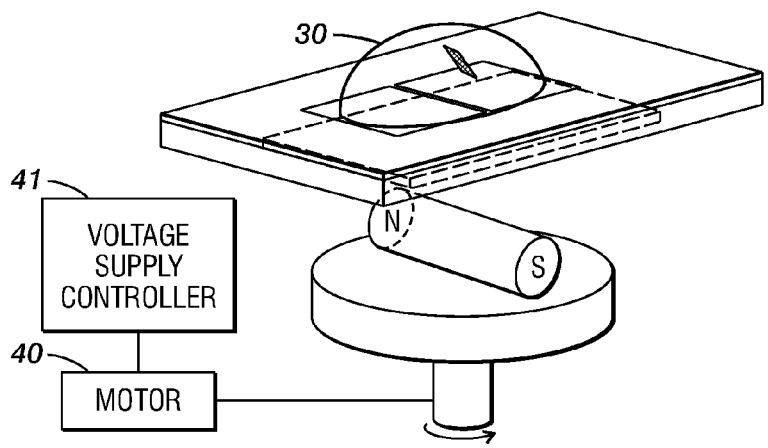

Turning to FIGS. 3A-3C an embodiment of the forgoing concept is illustrated. More particularly, FIG. 3A shows one of the drops 18 containing a small piece of magnetic material 32, in this embodiment, a rectangular bar or chip about 200 by 400 microns wide and long and 15 microns thick. The bar consists of a material such as Metglas® 2714A, a cobalt based amorphous metal from Metglas, Inc. of Conway, S.C. This class of metal is a soft ferromagnetic (i.e. it has high magnetic permeability with low remanence) with one of the highest known magnetic D.C. permeability values (e.g., the specified maximum relative magnetic permeability (DC) of Metglas® is $10^6$). It is understood that the magnetic material is not limited to this particular type of material, but can consist of a wide variety of materials that have magnetic properties, such as paramagnetic, superparamagnetic, ferromagnetic, ferrimagnetic properties, among others.

The bar has been deposited on the nanocalorimeter detector (14,16) prior to deposition of the drops 18 and 20. Underneath the nanocalorimeter detector a varying magnetic field is applied by a varying magnetic field generator 34. As shown in FIG. 3B this is accomplished by spinning or activating a magnet 36, such as a neodymium-based rare earth permanent magnet (NdFeB), mounted on a rotor 38 which is driven by a motor 40 energized and controlled by a voltage source and controller module 41. Upon application of this rotating field, the bar goes into suspension within the drop creating fluid motion inside the drop. Then, as depicted in FIG. 3C, voltage pulses are applied to the detector's electrodes (as in FIG. 2) via a voltage source controller mechanism 42, to merge the two drops together as drop 30, via electrostatic actuation. The stirring action of bar 32 enhances the mixing, by reducing the length scale over which the two reagents originating from drop 18 and drop 20 need to diffuse inside the merged drop 30 before they come in contact with each other. With attention to the concept of the length scale of diffusion, it may be considered that in the two drops shown in FIGS. 3A-3C reagents within the drops include molecule groupings A (e.g., in the left drop) and molecule groupings B (e.g., molecules in the right drop). There will be at least some of molecule A group at the furthest point from molecules of group B in the right drop. Therefore, in the absence of any applied external mixing mechanism, the molecules will need to diffuse by at most one half the size diameter of the merged drop (e.g., drop 30) to meet each other. So in this case the length scale of diffusion is the average distance between the group of molecules A and the group of molecules B within the merged drop. The magnetic stirring mechanism creates internal, rotational fluid flow inside the merged drop which effectively shortens this length scale. A time constant can be associated with the mixing speed using the equation in paragraph [0035] if the length scale is known and vice versa.

Figure 4:
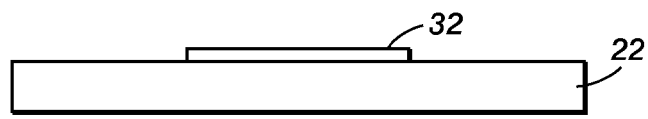
FIGS. 4-9 depict a more detailed view of the operation of a drop having a magnetic particle incorporated therein according to the teachings of the present application.
Figure 5:
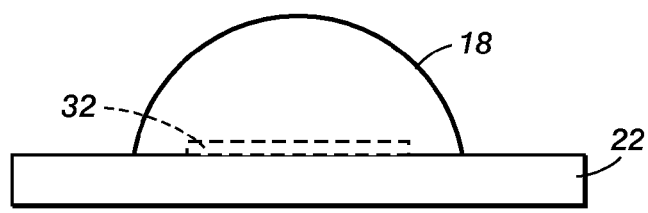
Figure 6:
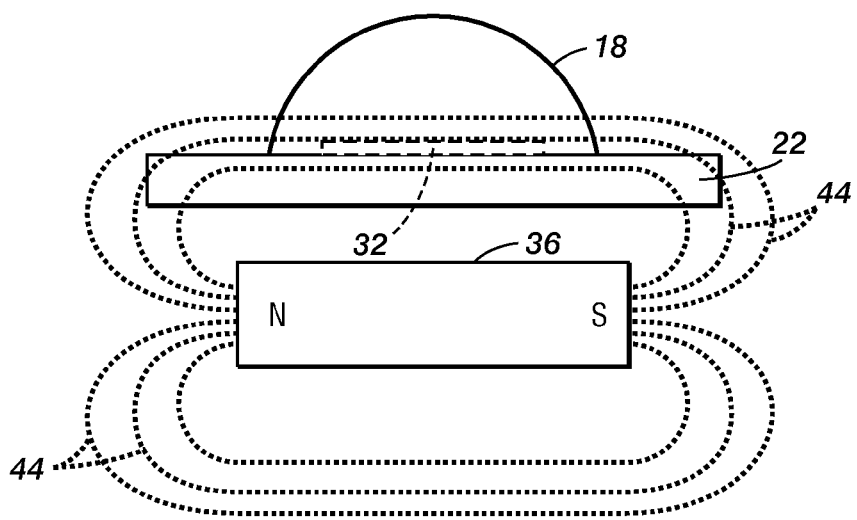
Figure 7:
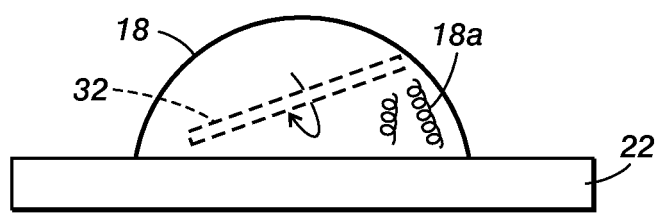

FIGS. 4-9 show more detailed views of the suspension and stirring action of bar 32 in drop 18. In FIG. 4 bar 32 is in contact with surface 22. In FIG. 5 drop 18 has been deposited at the location of bar 32 whereby the bar is at least partially within the drop, but still located on the surface. Then, as shown in FIG. 6, when the rotating magnet 36 is brought in proximity to the backside of the detector (14,16), the bar aligns itself to magnetic field lines 44. Then with the magnet spinning (at about 1500 rpm, in this example), and as shown in FIG. 7, the previously settled bar becomes suspended in the drop of fluid. The varying magnetic field causes the suspended bar to move within the drop resulting in a stirring action and internal fluid movement 18a.

Figure 8:
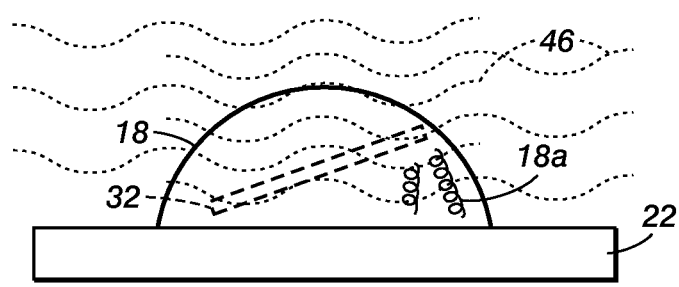
Figure 9:
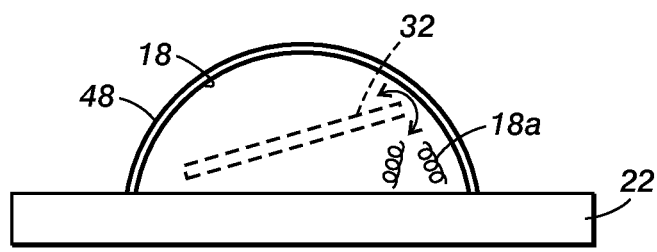

Turning to FIG. 8, illustrated is a drop in accordance with present concepts, in an embodiment where the drop has a liquid-solid interface (e.g., the interface between the drop and substrate) and a liquid-liquid or liquid-gas interface. More particularly, in this embodiment and as previously described, the nanocalorimeter operations may take place where the drops are submerged within a liquid or gas environment 46. In this situation, the drop 18 and liquid or gas 46 where the drop would be immiscible to the liquid and/or gas. Further, with attention to FIG. 9, shown is an embodiment where the drop 18 has a thin liquid film (such as a coating of oil) 48 on its entire surface.

To examine and verify effectiveness of the described device and method Fluorescent Resonant Energy Transfer (FRET) experiments have been performed. Results are summarized in emission graph 50 and table 52 of FIG. 10.

FRET is an effective technique to quantify mixing dynamics, as in principle the number of detected photons at the FRET emission wavelength increases when there is a binding event. This is true because non-radiative energy transfer between two fluorophores that are tagged to the reagents (material/particles in fluid) can only occur when the latter two are within molecular distance from each other.

The reagents in the FRET experiment need to be chosen such that the speed of the reaction itself is not limiting the rate of binding, but rather the mixing. Also, they need to be available with an appropriate set of fluorophores (i.e. with appropriate absorption and emission spectra, and a FRET emission spectrum that can be easily filtered out).

The FRET materials used in this instance consist of two DNA oligonucleotides: Alexa 555-5'-TTGGTGATCC-3', with peak absorption at 555 nm and peak emission at 570 nm;

and Alexa 647-5'-GGATCACCAA-3', with peak absorption at 650 nm and peak emission at 670 nm. The absorption spectrum of the latter shows minimal overlap with the emission spectrum of the former, hereby avoiding the generation of 'false positive' photons. The Alexa 647 fluorophore will only emit (at 670 nm) when the two DNA oligonucleotides are bound.

Figure 10:
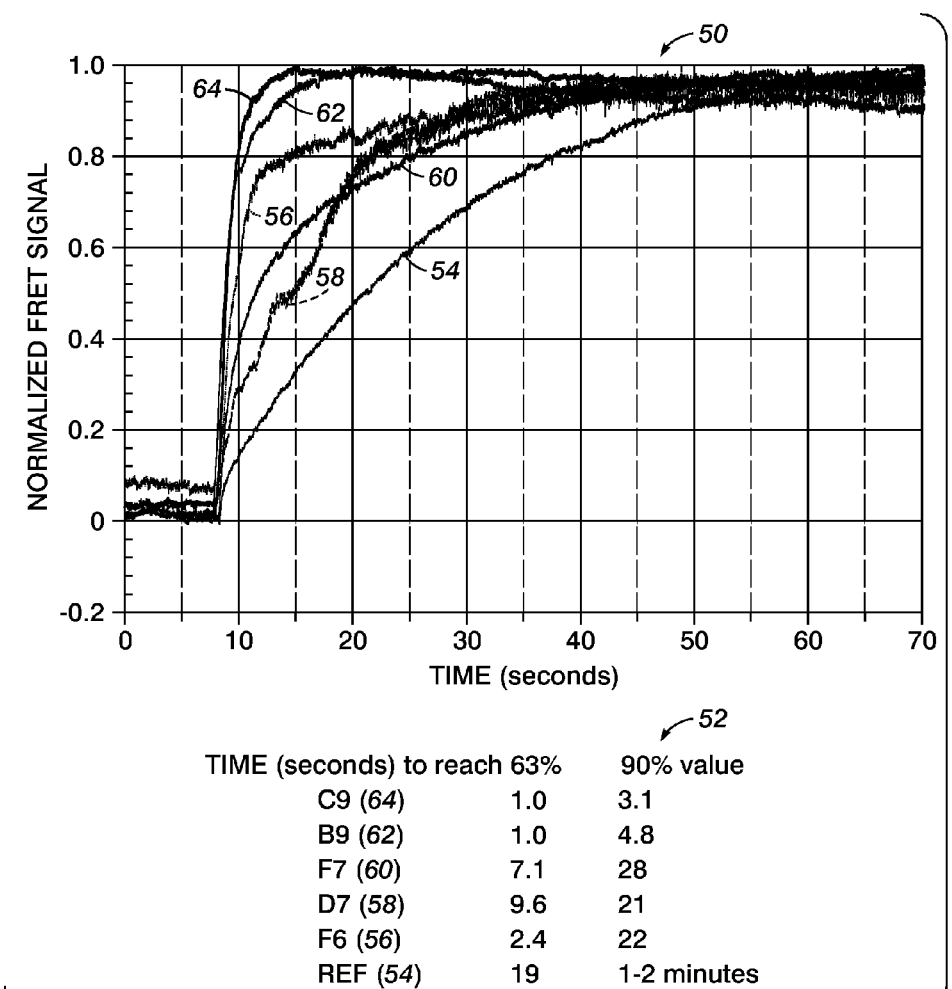
FIG. 10 shows a chart giving a summary of FRET data in the use of a magnetic material mixing concept.
Figure 11:
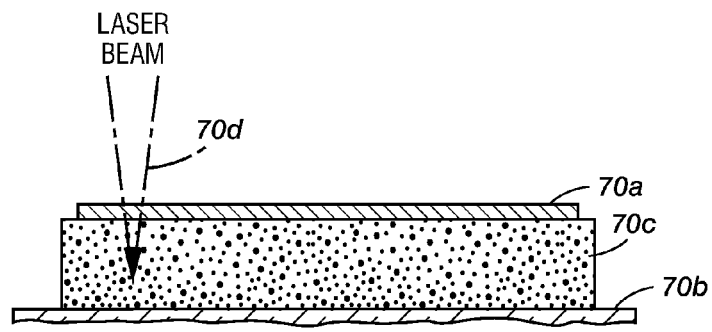
FIGS. 11-21 show a bar fabrication process.
Figure 12:
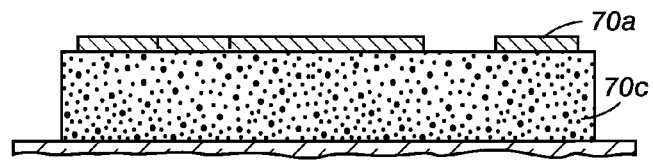
Figure 13:
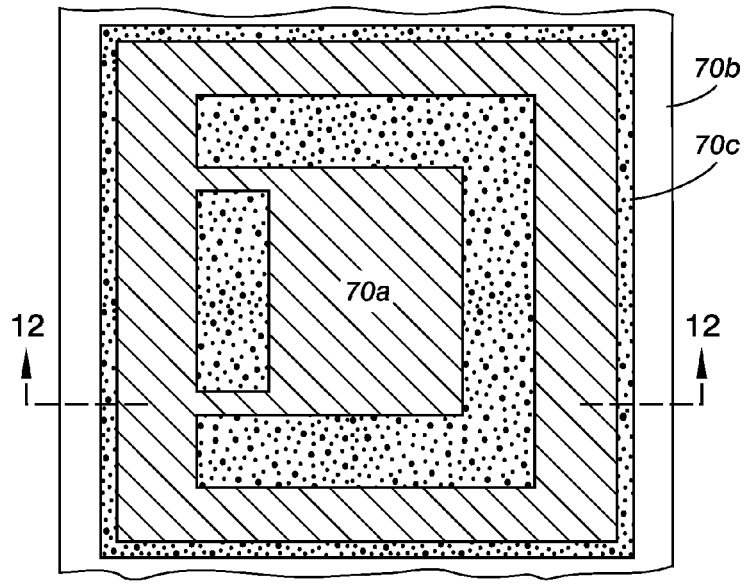

The light was measured using a photomultiplier tube (PMT) and a filter at 670 nm. The data shown in FIG. 10 is normalized with respect to the maximum amplitude of the FRET signal, as the latter may vary in different experiments (e.g., because of small changes in the alignment of the PMT, etc).

Data trace 54 depicts a control experiment with two drops without magnetic materials in them (i.e., no magnetic mixing) and as can be seen, the time constant is about 20 seconds, with full mixing not even achieved after 2 minutes.

The other traces 56-64 depict experiments with bars in one drop and magnetic stirring, with the motor spinning at 1500 rpm (except in the case represented by trace 62, which was stirred at 600 rpm). More specifically C9 used a single Metglas® 2714A bar and D16 type magnet, as acquired from K&J Magnetics, Inc. of Jamison, Pa.; B9 used a single Metglas® 2714A bar, at 600 rpm and 0.1 mg/mL bovine serum albumin (BSA) and D16 magnet; F7 and D7 used a single Metglas® 2714A bar, 1 mg/mL BSA and D24DIA magnet; and F6 used a single Metglas® 2714A bar, 1 mg/mL BSA and yet another type of magnet (AlNiCo). The experiment with stirring (C9) represented by trace 64 is indicative for the improvement in mixing speed. The time constant for this example is now about 1 second. Note the data generally is a bit noisier because the moving bars scatter some light.

In the other experiments with stirring (represented by traces 56, 58, 60), BSA (bovine serum albumin) is added to the drops in varying concentrations, in order to mimic the effect of 'sticky' proteins. Another variable is the type of magnet used, as indicated.

As can be seen, in all cases mixing is substantially improved, with some room for optimization in the case of highly sticky materials.

In recently performed actual nanocalorimeter measurements (BaCl2-18-Crown-6, as well as enzyme reactions), a significant improvement in sensitivity could be observed.

Turning now to the fabrication of the bars, as mentioned Metglas® 2714A has been used to form the bars, although other materials may be used. This material is available in sheets or ribbons of approximately 15 µm to 18 µm thick and about 2 inches wide.

In one bar formation procedure the Metglas sheet is mounted on double sided adhesive UV-tape (the tape's adhesive breaks down upon UV-irradiation). Then a protective and easily removable coating such as photoresist is spun on the surface of the sheet. Next, the material is diced, using a conventional wafer dicing saw, into rectangular dies (i.e., bars) of the appropriate dimensions. UV-irradiation and immersion into acetone or a similar solution are then performed to remove the UV-tape and the top photoresist layer, and the individual bars are collected. Sonication in acetone and cleaning in acetone/isopropyl alcohol/water is performed to remove debris from the edges of the collected bars.

In another bar formation process the Metglas sheet is mounted on UV-tape and patterned using a laser micromachining tool, such as one which uses a 266 nm tripled Nd:YAG laser system. The sheets are again coated with photoresist, to prevent recast of ablated material. Afterwards, UV-irradiation and cleaning in acetone are performed to release the bars. Advantages of the laser tool include its flexibility and cleaner finish (less edge debris).

Bars formed by the above techniques consist only of the amorphous magnetic metal material. This raises some concerns when the bars are immersed in drops containing biomaterials. One particular issue is the possibility that materials from the bars (e.g., metal atoms or ions) may dissolve into the drop, potentially causing problems such as poisoning enzymes. Another issue is that proteins may adsorb to the surfaces of the bars, resulting in less biomaterial available for the reaction.

With respect to the second issue the surface area a bar presents is on the order of the wafer surface the drop comes into contact with during the detection process. As the latter is not considered to cause significant problems, it is considered the additional surface area of the bar won't do so either. Nevertheless, to address concerns that for some applications adsorption may an issue, coating of the bars with appropriate materials is considered an operation that will act to reduce the potential of adsorption.

Coating the bars also addresses the first issue (i.e., metal dissolving into the drop). Several methods to coat the bars have been demonstrated, and are set out below.

Figure 14:
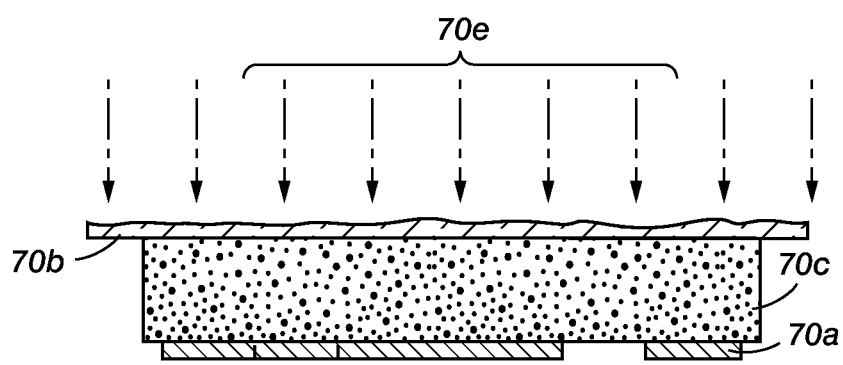

Turning initially to FIGS. 11-21 depicted is a process to fabricate coated magnetic bars. In a first step, a sheet or ribbon of amorphous magnetic metal approximately 15 µm in thickness (e.g., such as the previously mentioned Metglas) 70a is held to a glass substrate 70b via a piece of UV tape 70c, which may be approximately 100 µm thick. A laser 70d such as a 266 nm Tripled Nd:YAG laser system may be used to pattern the Metglas 70a into the form shown in FIGS. 12 (side view) and 13 (top view). Then, as depicted in FIG. 14, the assembly is exposed to UV light via lighting system 70e through the backside of glass substrate 70b to remove the bonds between Metglas sheet 70a and UV tape 70c, such that the Metglas sheet may be peeled from the tape. Thereafter, the Metglas sheet is cleaned, such as by sonication in acetone, rinsed with acetone, isopropyl alcohol and water, and then dried at 60° to 80° C. A subsequent oxygen plasma cleaning step (for instance 2 minutes at 200 W at 200 mTorr partial oxygen pressure) can be undertaken to further clean the surface of the material.

Figure 15:
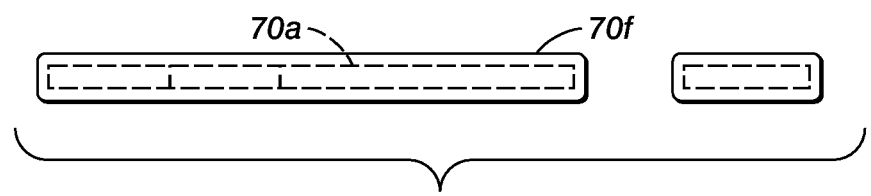

Next, in the step of FIG. 15, a PECVD process is undertaken to coat the Metglas sheet 70a with a conformal layer of silicon oxynitride (SiON) (the coating is designated by 70f). FIG. 15 is also intended to represent a sputtered silicon oxide coating process, or other coating process which may be appropriate.

Figure 16:
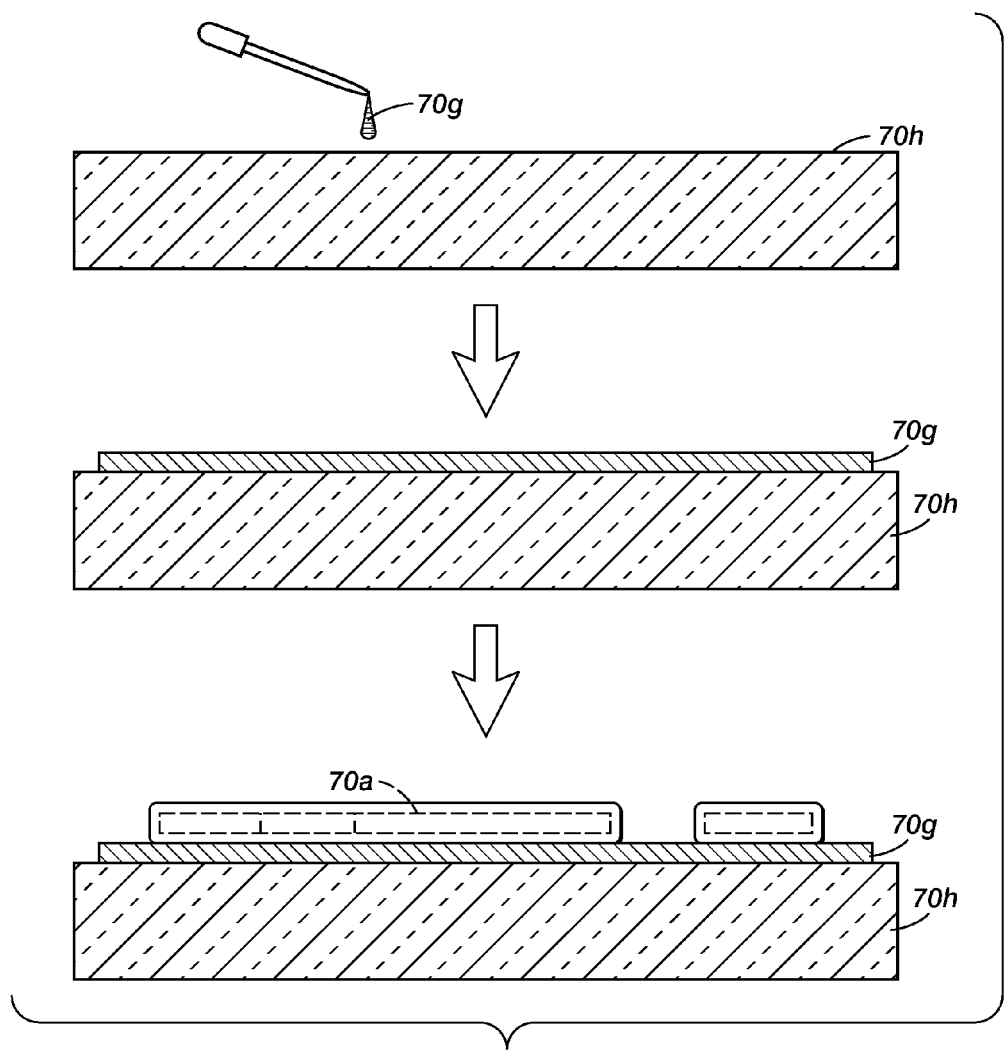

Thereafter, in the step of FIG. 16, photoresist 70g is spun on a glass substrate 70h, and the SiON coated Metglas strip 70a is mounted on the photoresist layer 70g. This arrangement is then baked for approximately ten minutes at 90° C.

Figure 17:
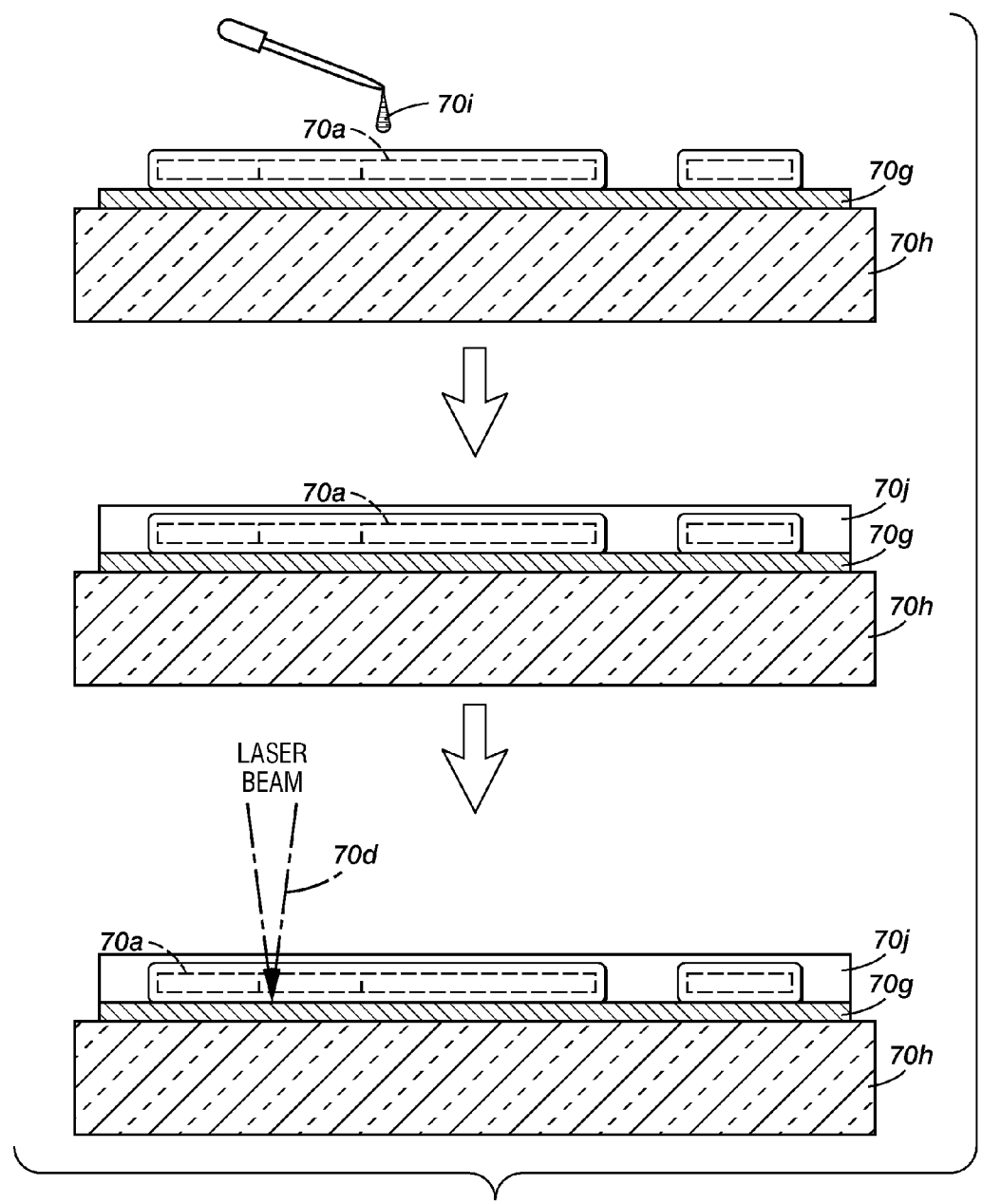
Figure 18:
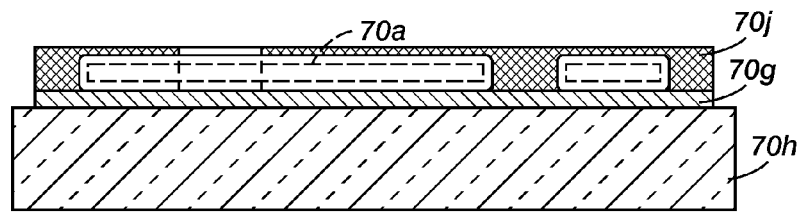

Turning to the step of FIG. 17, another layer of photoresist 70i is spun onto and over the coated Metglas sheet 70a, and then again baked for approximately ten minutes at 90° C. At this point, the laser 70d is used to make an additional laser cut to pattern the Metglas sheet 70a to form a bar, the patterned SiON and photoresist coated Metglas sheet 70a being shown in FIG. 18.

Figure 19:
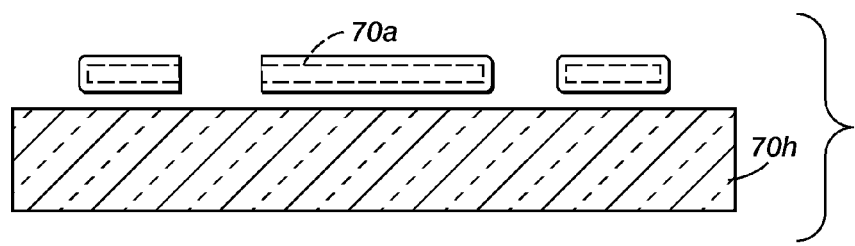
Figure 20:
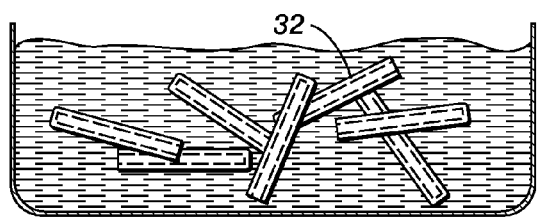

In the step of FIG. 19, the photoresist is rinsed away with an appropriate solvent such as acetone. Thereafter, the patterned Metglas sheet, in the form of the bar 32, is solution coated with polyethylene glycol (PEG), as shown in FIG. 20. The use of the PEG coating improves the reliability by which the bar, when inside a drop, overcomes friction and other surface forces upon application of the magnetic actuation; without this coating, it may in some cases remain stuck to the surface.

The PEG coating process is undertaken in multiple steps. In an initial step the bars are cleaned, with a rinse in 50% sulfuric acid and a subsequent rinse in de-ionized (DI) water. Next, the bars are dried and put into a container such as a vial or other fluid holding structure. Thereafter added to the vial is a mixture including 20 ml of toluene, 20 microliters of hexylamine, 0.054 g of a PEG solution (such as "mPEG silane 1 kDa", from Creative PEGworks of Winston Salem, N.C.). The mixture in the container (e.g., vial) is mixed for approximately 2 hours or more. In one embodiment, the mixing may be accomplished by placing the vial in an end-to-end rotator. Thereafter, the toluene is decanted, then the bars are rinsed in toluene, acetone, isopropyl-alcohol (IPA), and then finally rinsed again in de-ionized (DI) water. Finally, the bars are dried and the coating process is completed. A more detailed discussion of surface modification using PEG (poly(ethylene glycol) is set forth in the article by Seongbong Jo and Kinam Park, Surface modification using silanated poly(ethylene glycol)s, Biomaterials Volume 21, Issue 6, March 2000, Pages 605-616, incorporated herein in its entirety.

Figure 21:
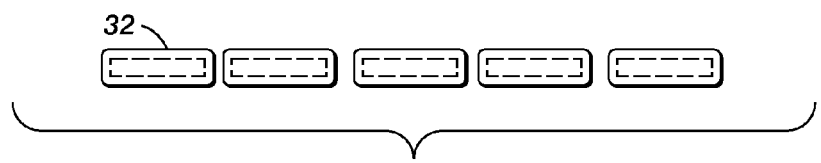

FIG. 20 also shows multiple bars, each formed by the described process. Finally, FIG. 21 shows the PEG coated bars being dried.

In another bar fabrication process, the Metglas sheets are coated using a PECVD system with silicon oxynitride, silicon dioxide or silicon nitride, before patterning. Optionally, they are coated with an additional layer of parylene-C (using a silane-based adhesion promoter to ensure good adhesion of the parylene). The conformal parylene coating will plug any small hole or defect in the underlying layer.

Still other coating process may be used to coat the edges entirely. For example, parylene coating the bars may be undertaken after they've been released from a substrate. In this process, the bars are kept suspended or in motion during parylene deposition, such that all surfaces are exposed. This can be achieved by means of a mechanical (tumbler), magnetic or ultrasonic agitation system embedded inside the parylene reactor.

Figure 22:
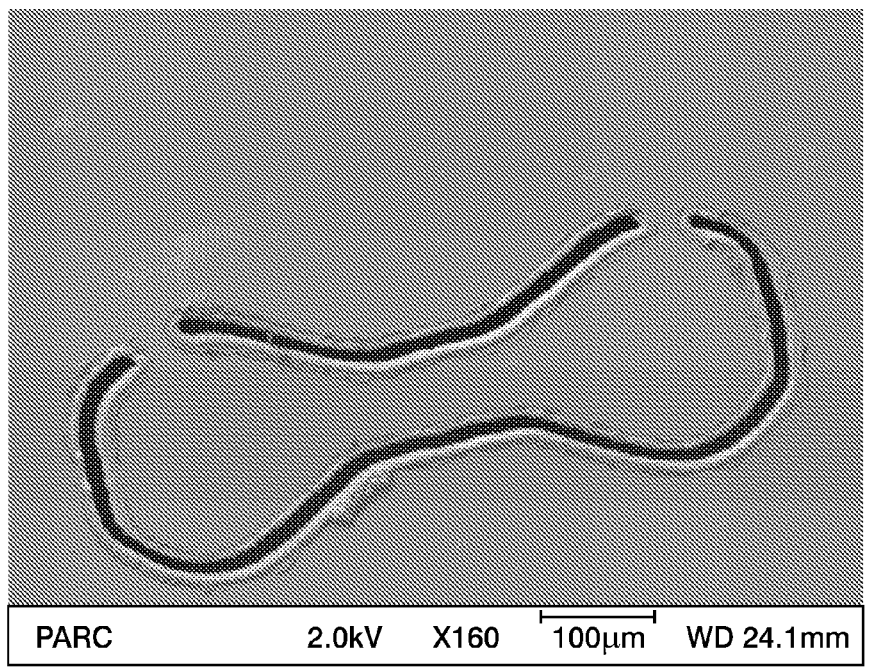
FIG. 22 illustrates a SEM image of a partially laser machined bar.
Figure 23:
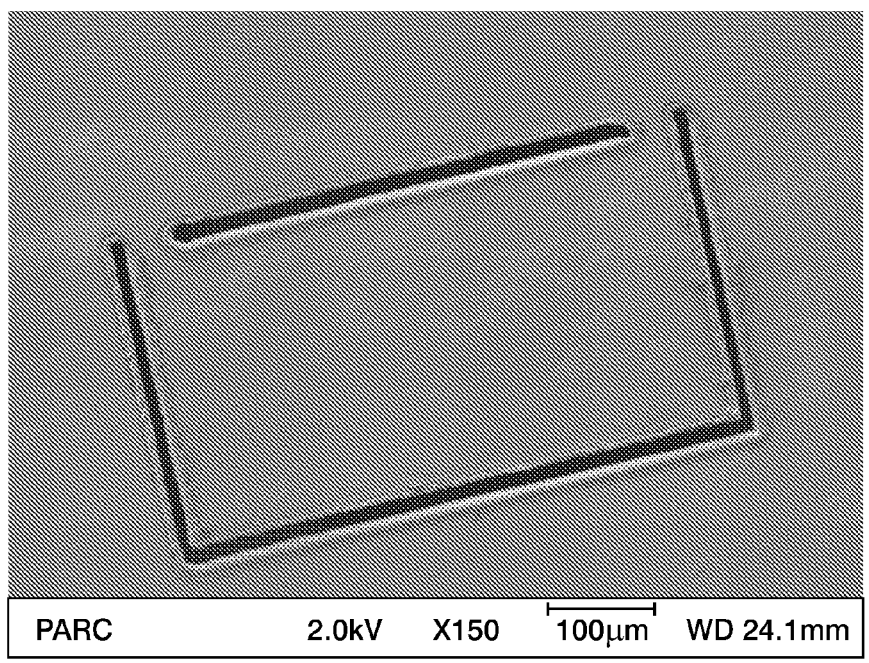
FIG. 23 illustrates another SEM image of a partially laser machined bar.

Turning to FIGS. 22 and 23 shown are images of partially laser machined structures according to a process such as described and illustrated by FIGS. 11-21. FIG. 22 illustrates a non-rectangular structure from which a bar is formed, while FIG. 23 shows the structure from which the bar is formed is in a rectangular shape. As in the previously described concepts the bars are laser machined from the Metglas sheet while leaving small attachments or bridges intact, keeping the bars attached to the surrounding material. The sheets are then conformally coated with silicon oxynitride and parylene. In a second laser machining step, the bridges are cut and the bars released. Using this process the bars are entirely coated, except for a very small section (about 20 μm long). The exposed surface area is reduced by more than two orders of magnitude. FIGS. 22 and 23 are provided to emphasize the described process in FIGS. 11-21 may be applied to form the bars in any of a number of geometric shapes.

It is to be understood that steps in the various bar manufacturing processes may be used within other ones of the described processes. In addition to the different fabrication manufacturing techniques, it is understood materials other than Metglas® 2714A can be used, as well as bars of different dimensions, geometry or shape. It is noted a different bar geometry may result in different flow patterns, and potentially faster mixing. Also a bar consisting of a hard ferromagnetic material (with high remanence) may have uses, as the bar is then a small permanent magnet, which may have improved stirring characteristics.

Once the bars have been fabricated it is necessary to place the bars in a position where a drop can be deposited. Bars are deposited on the nanocalorimeter detectors using simple pick-and-place techniques in low- or medium-throughput modes of operation. This can be done manually, using fine tweezers or vacuum tweezers, or by a pick-and-place machine such as the West-Bond model 7372E from West-Bond, Inc. of Anaheim Calif.

Employing one of the above techniques a bar is positioned above one of the drop merge electrodes of a detector. Once in place, the reagent drops of fluid are deposited onto the drop merge electrodes, at least one of them on top of the bar. Depositing the drops have been performed manually (by using syringes) as well as by the Deerac Spot-on™ liquid dispensing system from Deerac Spot-on of Dublin, Ireland. It is noted that in experiments, the presence of the bars did not appear to interfere with the dispensing system or impede accurate drop placement. Also, surface forces and/or stiction appeared to be sufficient to hold the bars in place during the simple wafer handling operations prior to the deposition of drops.

Figure 24:
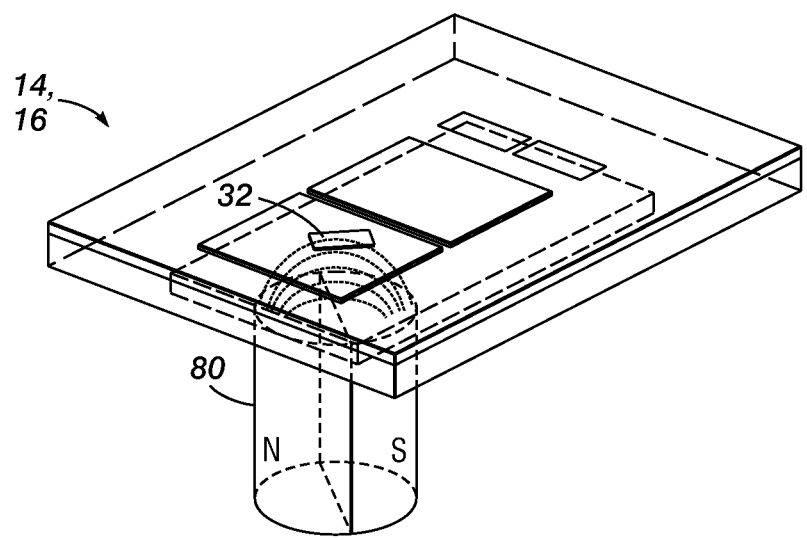
FIG. 24 depicts a permanent magnet underneath a detector to hold micro-bars in place.
Figure 25A:
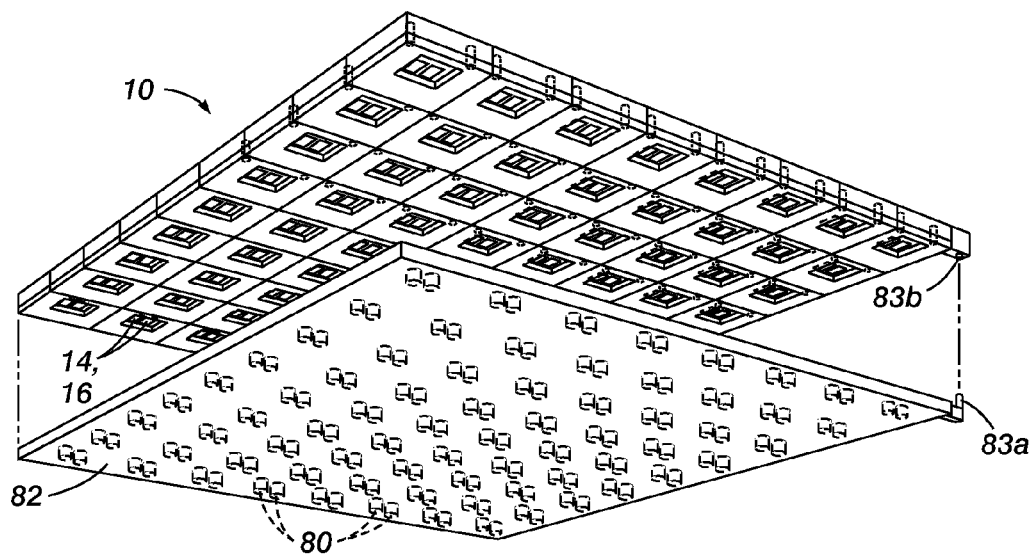
FIGS. 25A-25B set out a fixture with permanent magnets as an array handling tool.
Figure 25B:
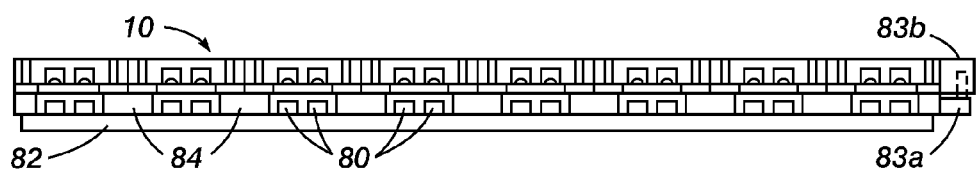
Figure 26:
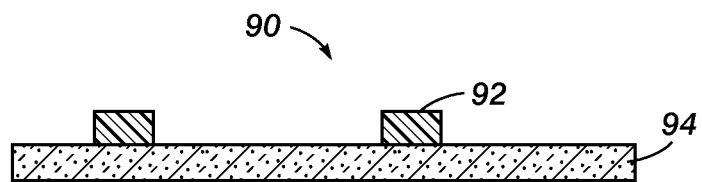
FIGS. 26-30 depict a micro-bar deposition and transfer technique.
Figure 27:
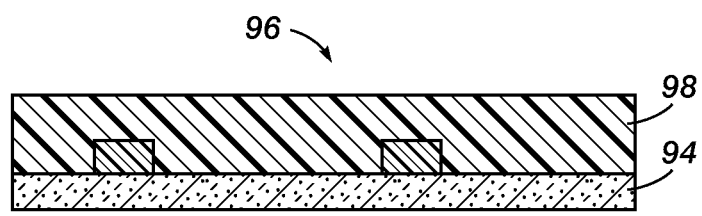
Figure 28:
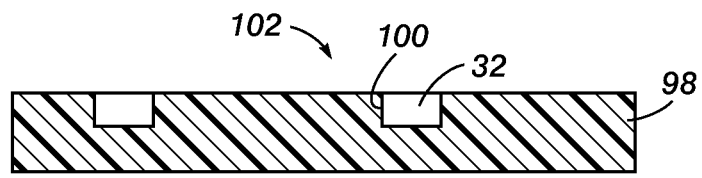
Figure 29:
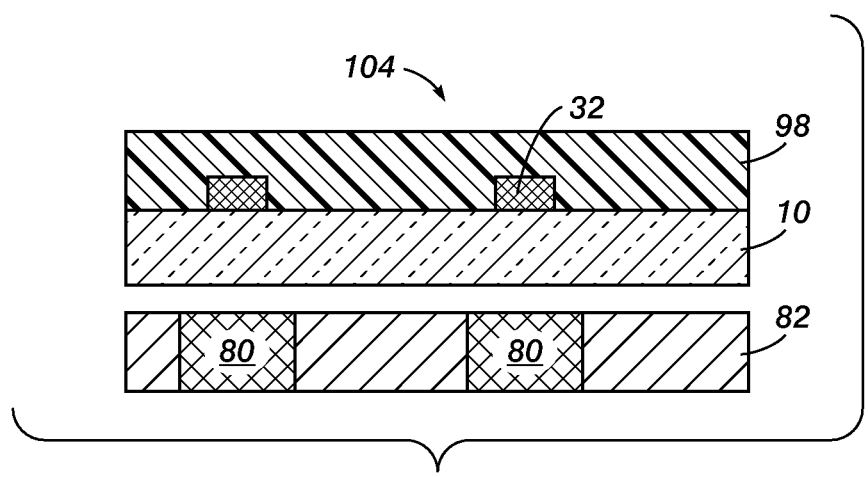
Figure 30:
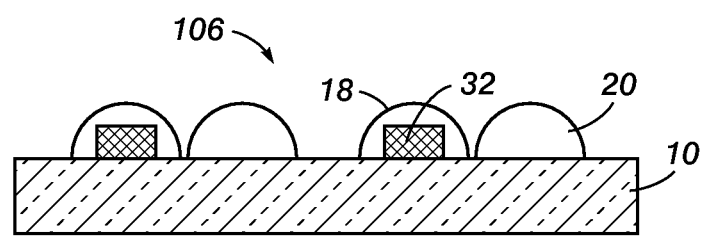

It is appreciated that benefits to the foregoing devices and methods may also be obtained when the concepts are employed in larger arrays (e.g., the 96-detector array, etc.). In view of this, it is noted a more scalable approach to placement of the bars can be achieved by implementation of the concepts shown in FIG. 24. In this design a magnet 80 is located underneath a detector (14 or 16) to hold bar 32 in place. Thus, the arrangement can be moved and the bar will stay in its aligned location. Employing this concept in association with a fixture 82, such as in FIGS. 25A-25B, expands the concept for use with arrays of detectors. In such a design magnets 80 are mounted on the fixture 82 so that they will be located underneath the array of nanocalorimeter detectors (14 or 16, e.g., of FIG. 24) when the fixture is associated with the array 10. More particularly, the mounted magnets protrude through openings in the stainless steel support part 84 of the array 10, allowing the magnets to be positioned in close proximity to the polyethylene naphthalate (PEN) membrane (not shown) of individual detectors, underneath the drop merge electrodes (see FIGS. 1A, 1B, and 2A-2C).

By properly aligning fixture 82 to the array and latching or connecting it in place, the fixture can be used both as an array handling tool as well as a tool to deposit and align the bars. The latching or connection of the fixture to the array can be achieved by sizing the fixture at dimensions that permit a snap type fit with the array. Another latching design would be to incorporate complimentary locking taps on the array and fixture on, for example, each component's outer periphery. For example, with attention to FIGS. 25A-25B, male tab 83a may be inserted into female connector 83b. A plurality of these along the outer edge of these components would provide the desired latching.

As mentioned, the fixture could be used as an array handling tool and a bar deposition tool. Turning first to its use as an array handling tool, when the fixture is in place, the bars are effectively held to the array by magnetic forces, and their positions are determined by the placement of the magnets. For example, if in one embodiment the magnets are cylindrical and diametrically magnetized, with a diameter equal to or less in size than the lateral distance between the two drop merge electrodes, the fixture design provides a simple and effective way to self-align the bars.

An experiment using a simplified prototype of such a fixture showed the bars are kept in place even when a pressurized nitrogen gun is employed to blow the wafer surface of the detector. Such an array handling tool can also be used in an automated system to deposit drops, apply caps (that control evaporation) and transfer the wafer to the measurement chamber without disturbing the bars.

With attention to FIGS. 26-30 illustrated is a procedure where the fixture 82 is used as a bar deposition tool for a package of bars 32. In this embodiment the fixture is used to transfer the array of bars from the package to a nanocalorimeter array 10 and subsequently maintain them in place. FIGS. 26-31 further illustrate how the package and the detector array may form a combined assembly that enables easy shipping and handling of arrays.

In a first step 90 an array of pillars 92 are formed on a substrate 94, such as a bare silicon wafer. The pillars are formed of a photoresist or other appropriate material, and have the same height/thickness as the bars (e.g., 15 µm). Then, in step 96, a 50 to 100 µm thick layer of flexible polymer or elastomer (such as PDMS, e.g., a mold) 98 is cast on the substrate containing the array of pillars 92. As shown in step 102 of FIG. 28, the pillars are used to create a pattern of wells 100 in the resulting flexible polymer mold 98, once it is removed from the substrate 94. The wells 100 are then filled with bars 32, as shown in step 104 of FIG. 29. The placement of bars 32 into wells as shown in step 104 may be achieved by alternative arrangements. For example, pick-and-place techniques or magnetic self-assembly techniques, etc., may be used. Alternatively, the bars could be formed in place from a sheet of the amorphous magnetic material (e.g., a Metglas sheet) placed on top of the mold and patterned using a laser micromachining tool. Step 104 further shows the flexible polymer mold 98 with the bars 32 aligned and attached to the enthalpy array 10.

The flexible polymer should be selected such that no residue is left behind on the array. Alternatively the mold could be coated with parylene or other appropriate material to obtain this behavior.

In step 104 the magnetic fixture 82 is positioned below the array whereby the magnetic forces exerted by the magnets align and hold the bars 32 to the surface of the array 10. At this point, the mold is peeled off, leaving the bars in place on the array, and ready for the application of the drops of fluid as in step 106.

As mentioned, placement of bars 32 into wells of the mold 98 as described in step 104, may be achieved by pick-and-place techniques or magnetic self-assembly, among others. In one embodiment, the magnetic self-assembly technique would have a mold such as depicted in step 102 of FIG. 28 wherein the magnetic stir bars 32 have not yet been incorporated into the wells 100. A plurality of the bars are disposed generally on the upper surface of mold 98 and the mold is made to vibrate, moving the bars. Then a magnet array such as 82 of step 104 is placed underneath the mold. Vibration of the mold 98 and the magnetic attraction of magnetic array 82 is used to attract the moving bars (i.e., by the shaking process) into wells. Once the wells are filled with bars, vibration is stopped and the magnet array is removed.)

Figure 31A:
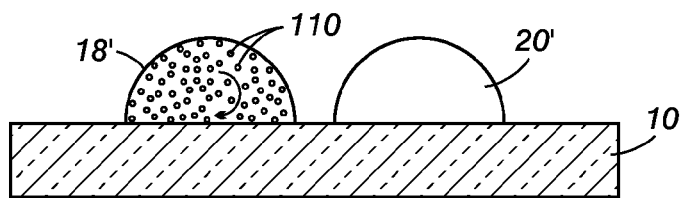
FIGS. 31A-31B illustrate a drop merging process wherein the magnetic materials are particles or beads.
Figure 31B:
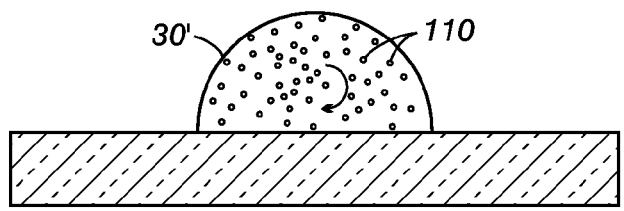

While the forgoing discussion has focused on the use of bars as the magnetic material suspended in the drops, other configurations could be used including, as illustrated in FIGS. 31A and 31B, magnetic particles or beads 110 suspended in drop 18', where drop 20' has no particle or bead. Fast mixing with particles or beads has been demonstrated by FRET experiments using silicon oxide coated carbonyl iron powder (where one such product goes by the name: 'EW-I beads', distributed by BASF AG headquartered in Ludwigshafen, Germany). Mixing was found to be as fast as in the case of the bars (1 to 2 seconds time constant), for bead concentrations of roughly 10 mg/ml at 1500 rpm stirring speed. It is to be appreciated that while FIGS. 31A and 31B show a plurality of beads, these beads are very small, i.e., in the micron range, and in many embodiments thousands of such beads may be suspended in a freestanding drop in order to produce the mixing speed which is desirable. Therefore, the particles 110 shown in these figures may be many more than are illustrated.

One issue with the use of particles or beads that because of their large surface area the particles or beads need to be coated with a surface coating that significantly limits protein adsorption, such as PEG (polyethylene glycol). In addition to that, such coating needs to prevent material from the beads (e.g. metals) to dissolve into the drops and possibly interact with the biomaterials. This concern is also true for the Metglas® 2714A bars (in the latter case the bars are passivated by for instance a conformal oxynitride or parylene coating, as mentioned earlier).

Figure 32:
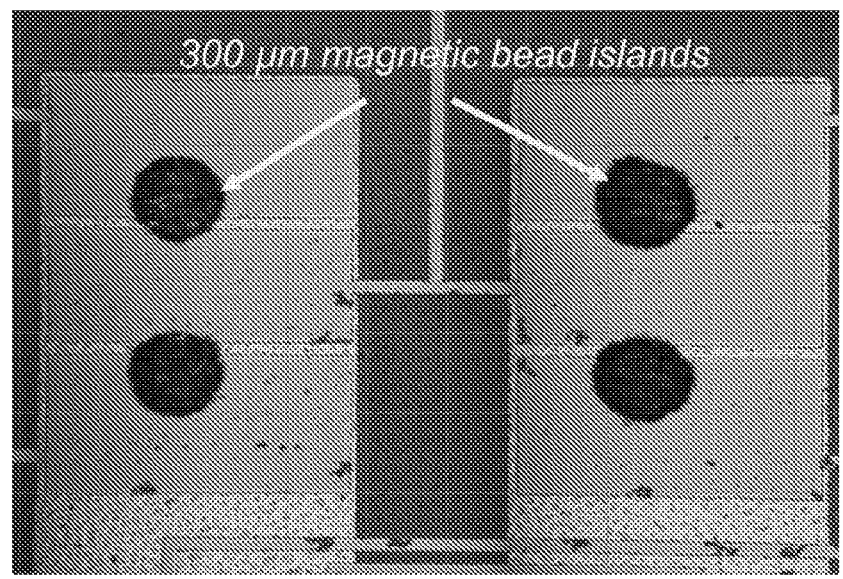
FIG. 32 sets forth a screen printed magnetic bead configuration.

To obtain a controllable amount of particles or beads in the drops, the particles or beads are first deposited on the wafer/substrate surface of the detector. Subsequently, the drops are deposited and the particles or beads re-suspend when the rotating magnetic field is applied. This has been demonstrated using EW-I bead type particles, that were deposited on the array using a screen printing technique and a thin PEN stencil 112, as depicted in FIG. 32.

Figure 33:
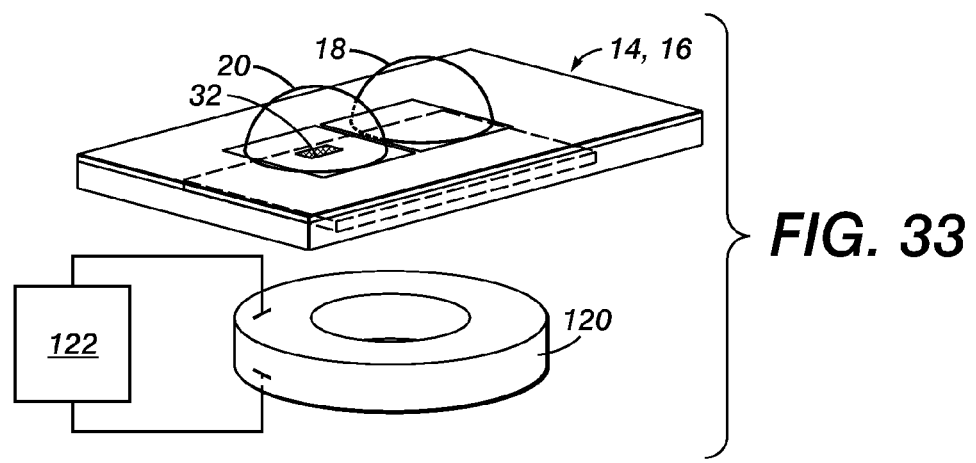
FIG. 33 illustrates a system according to the present concepts using electromagnets.

While generation of the external magnetic field described herein has focused on the spinning of permanent magnets at a constant speed, the field can be generated by alternative designs. For example, as depicted in FIG. 33, an assembly of electromagnets (e.g. coils) 120 powered and controlled by a voltage supply and controller mechanism 122, may be used to generate the external magnetic field. Using this design, allows for instance, a multi-pole magnetic geometry to generate more complex varying field patterns than obtained by the spinning permanent magnet implementation.

In another arrangement the motor driving the magnet can be driven by a non-sinusoidal signal or ramped-up slowly instead of switched on and off as controlled, for example, by the voltage source and controller mechanisms 41 and 122 of FIGS. 3A-3C and 33.

Using these arrangements can make mixing even faster as these implementations can create a more complex stirring pattern of the bar or beads induced by these external forces, and further reduce the length scale of mixing. In addition, these actions can improve the process of suspending the magnetic bar or beads in drops containing highly sticky materials where surface forces may otherwise prevent the suspension. For example, abrupt changes in the applied magnetic field may work to overcome the forces holding the bar to the surface. Also, controlling of the field may allow the focusing in on a bar's resonant frequency to increase movement of the bar.

In another embodiment the magnetic field generated by either a permanent magnet or an electromagnet may be controlled by voltage source and controller mechanisms 41, 122, where one mode of magnetic actuation is used to trigger the actuation of internal stirring of a drop, while another mode is used to move the drop to obtain the merging of the drops—this would remove the need for an electrostatic drop merging mechanism in the device.

In the foregoing discussion, the described procedure has been that the magnetic materials (i.e., the bars and/or beads) are placed on the substrate. However, it is to be appreciated there may be embodiments where the magnetic materials are formed on a substrate. For example, they may be formed onto the substrate and connected to it by a layer of adhesive material. Suspension of the bar or beads can be achieved by having the adhesive being water soluble and otherwise inert such that addition of a drop will allow the re-suspension of the bar or beads. It is to be understood that even when the bar or beads are formed on the substrate they are to still be considered to be placed on the substrate.

Certain embodiments of the foregoing description teach internal mixing of the drop of fluid by magnetic mixing may take place while the drop is being moved. In other embodiments, the mixing may take place in a non-moving drop. In still other embodiments, the internal mixing by the magnetic material continues after drop merging. In yet a further embodiment, the internal mixing starts after the drops are merged. It is also to be understood that in various embodiments, the magnetic material may be in only one drop, and in other embodiments magnetic material may be in both drops.

Still further, the previous discussions have also emphasized the concept of placing the magnetic material and then adding the drops of fluid. However, it is to be appreciated that in some embodiments, using the appropriate devices, the drop of fluid may be deposited prior to the magnetic material so the magnetic material is placed into the drop. In this instance, the force of magnetic attraction would still cause the magnetic material to move inside the drop. Therefore the mixing concepts of the present application would still be useful.

It is to be appreciated, that in still a further embodiment, placement of the magnetic material and placement of the drops, may be at locations where the drops do not result in the first magnetic material being within the first or second drops. In these embodiments, the magnetic material may be placed in front of, for example, where one of the drops shall be made to move by the drop merging operation. In such an embodiment, as the drop being made to move by the merging operation, it moves over the magnetic material location, thereby resulting in the magnetic material being within the drop of fluid. Then when magnetic material is within the drop of fluid, a varying magnetic field may be used to move the magnetic material within the drop, causing internal stirring as previously described. Of course, in alternative embodiments, this process may be used to cause magnetic materials to be placed within each of the drops.

Figure 34:
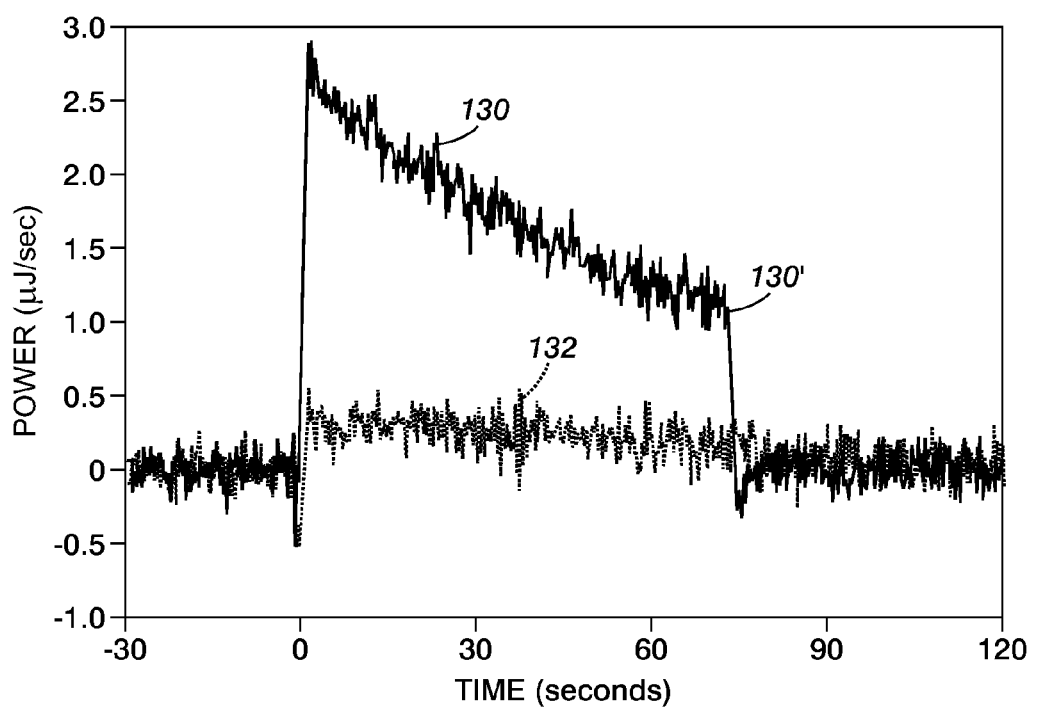
FIG. 34 illustrates traces of an enzymatic reaction.

Turning to FIG. 34, illustrated is a graph of power versus time, representing the output in enzymatic reactions for purely non-magnetic mixing versus magnetic mixing according to the concepts of the present application, wherein non-magnetic mixing is the mixing of fluid which occurs when drops are merged solely by electrostatic merging. More particularly, trace 130 shows the output from a nanocalorimeter detector when a magnetic mixing operation is performed versus trace 132, which represents the output from a nanocalorimeter operation for enzymatic reactions when electrostatic mixing is employed.

The power output is primarily obtained from the temperature measured by the thermistors. As this is an enzymatic reaction, the reaction will be measured for approximately a minute, which represents the continuous release of heat from the reaction. The graph shows the benefits of faster mixing, as less heat is being lost to the environment when magnetic mixing is used when compared to electrostatic mixing.

It is noted $K_M$ and $k_{cat}$ are the Michaelis constant and turnover number for the enzyme reactions. The graph of FIG. 34 also shows the use of magnetic mixing/merging allows for an easier estimation of $K_M$ and $k_{cat}$. Particularly, while $k_{cat}$ can be estimated at the beginning of both signals (i.e., at zero "0" seconds), the estimation using magnetic mixing trace 130 is more easily identified and estimated. Particularly, due to the loss of less heat at time 0, the signal obtained when magnetic mixing is used is five times greater than the signal for electrostatic mixing.

Additionally, $K_M$ which is a parameter determined near the end or downslope of a reaction (e.g., approximately at 70 seconds in this reaction), the magnetic mixing also allows for an estimation here as the downslope 130' is visually discernable. On the other hand, near the end of the reaction or downslope for the electrostatic mixing (i.e., at 70 seconds) it is not visually discernable. Therefore, while with magnetic mixing the $K_M$ can be estimated, it is not possible with electrostatic mixing.

Figure 35:
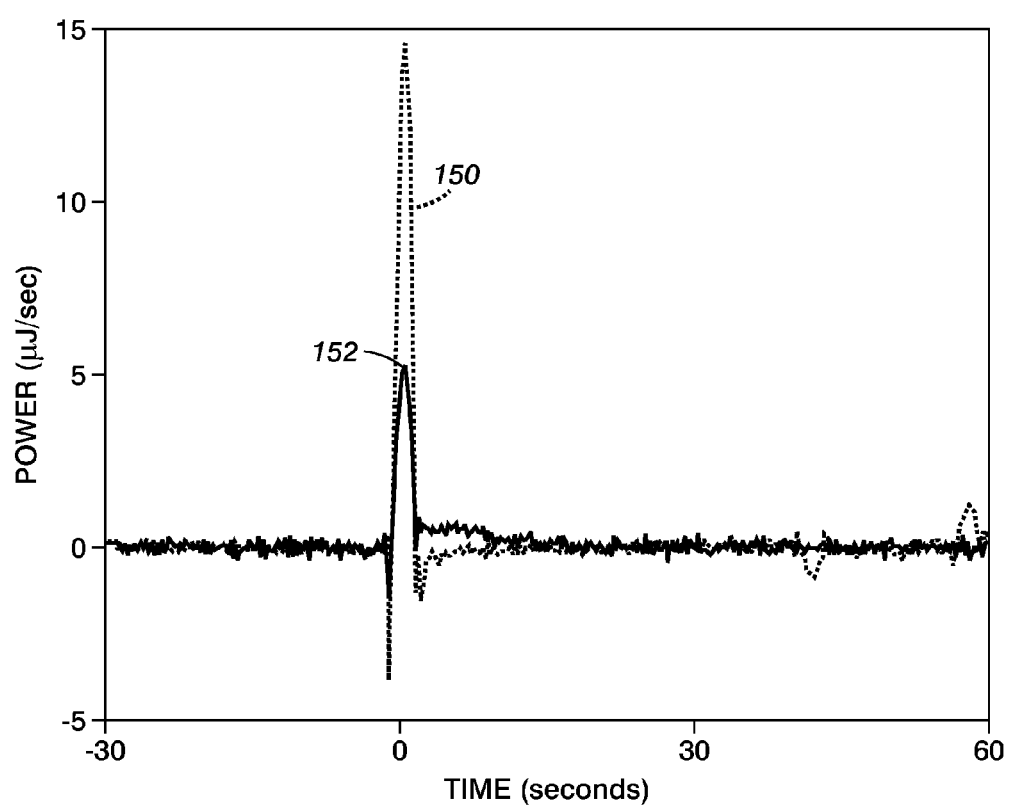
FIG. 35 illustrates traces for a binding action.

Turning to FIG. 35, illustrated is a chart which compares signal traces generated by magnetic mixing 150 and electrostatic mixing 152 for binding reactions, and shows that magnetic mixing significantly increases the signal to noise for binding reactions. In binding reactions, two substances are combined and a certain amount of heat is given off. This heat is detected at the peaks of traces 150, 152. Again, the larger peak signal of magnetic mixing trace 150 is achieved as less heat is lost to the environment due to the increased speed at which the drops are mixed.

Having described various structures and embodiments for constructing the foregoing devices and performing corresponding methods, it is noted that when the following three time constants in a nanocalorimeter measurement are considered Thermal dissipation time constant of the device
Mixing time constant, and
Duration of the reaction then 'slow' mixing can be understood to be mixing with a time constant that is larger than or of the order of both the duration of the reaction and the thermal dissipation time constant. In such case, heat is lost at about the same pace as it is being generated, and only relatively strong reactions will be detected. However, by employing the concepts described herein to increase the speed of mixing, will result in a sharper and higher temperature increase sensed by the thermistors, resulting in improved sensitivity.

The 'fast' mixing obtained by the described methods and devices means weaker binding reactions can be detected, due to the increased signals, which also allows full kinetic characterization of enzymatic reactions. More specifically, the achieved faster mixing allows determination of both $k_{cat}$ and $K_M$, cfr. the Michaelis-Menten model of enzyme kinetics. This means a broader range of biochemical assays can be performed by the nanocalorimeter detectors.

Preliminary BaCl2-18-Crown-6 measurements (a chemical reaction that is a predictable and useful mockup for a binding reaction) as well as enzyme measurements have confirmed the above.

Measurements have also showed that a number of potential obstacles can be negotiated successfully:

Excess electrical noise, caused by the motor, various inductive coupling mechanisms, mechanical vibrations etc: excess noise appears to be limited or manageable in performed experiments.

Thermal stabilization: a new array mounting block was designed and built to incorporate the motor and spinning magnets. This does not appear to lead to significant deterioration of the thermal stabilization properties of the block.

Excess evaporative or convective heat loss: the rapid motion of the micro-bar inside the drop does not appear to lead to excess evaporative or convective heat loss at the drop-air interface, at least not in a differential way.

Excess (ohmic) heating due to eddy currents generated by the time-varying magnetic fields does not appear to be an issue.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A method of mixing and merging a first drop of fluid and a second drop of fluid comprising:
    providing a nanocalorimeter device having a surface including at least a first location for supporting the first drop and a second location for supporting the second drop,
    placing a coated magnetic material at the first location on the surface, wherein the coating prevents reaction of the magnetic material with constituents of the first drop of fluid and constituents of the second drop of fluid;
    placing the first drop of fluid at the first location on the surface, resulting in the coated magnetic material being at least partially within the first drop of fluid;
    placing the second drop of fluid at the second location on the surface;
    initiating a drop merging operation by a drop merging mechanism of the nanocalorimeter device such that at least one of the first drop of fluid or the second drop of fluid are moved toward the other drop of fluid creating a merged drop including the coated magnetic material; and
    applying a varying magnetic field to at least a portion of the surface including at least the merged drop, the varying magnetic field acting on the coated magnetic material to move the coated magnetic material within the merged drop, causing an internal stirring of the fluid in the merged drop,
    wherein the application of the varying magnetic field to the coated magnetic material in the merged drop generates a kinetic reaction of the constituents of the first and second drops producing a temperature rise in the micro-Kelvin range that is detectable by the nanocalorimeter, and that is at least five times greater than a signal generated by drop merger in the absence of the varying magnetic field.

2. The method according to claim 1 wherein the coated magnetic material is in the form of a single magnetic bar.

3. The method according to claim 1 wherein the drop merging mechanism is based on electrostatic forces.

4. The method according to claim 1 wherein the drop merging mechanism is based on magnetic actuation.

5. The method according to claim 1 wherein the drops have a solid-liquid interface and one of a liquid-gas interface or a liquid-liquid interface.

6. The method according to claim 1 wherein the step of placing the first drop of fluid occurs before the step of placing the coated magnetic material.

7. The method according to claim 1 wherein the magnetic material is formed at the first location.

8. A device for detecting a heat of reaction in the micro-Kelvin range from a mixing of at least a first drop of fluid and a second drop of fluid, the device comprising:
    a nanocalorimeter device including a surface having a drop merging area, including a first location for receipt of a first drop of fluid and a second location for receipt of a second drop of fluid;
    a coated magnetic material positioned at the first location, wherein the coating prevents reaction of the magnetic material with constituents of the first drop of fluid or constituents of the second drop of fluid;
    a first drop of fluid at the first location;
    a second drop of fluid at the second location;
    a varying magnetic field generator, configured to generate a varying magnetic field for application to the coated magnetic material; and
    a drop merging mechanism configured to move at least one of the first drop of fluid and the second drop of fluid towards the other drop to create a merged drop, wherein a signal detectable by the nanocalorimeter device results from reaction of constituents of the first drop of fluid and constituents of the second drop of fluid when merged, the reaction being a result of a combination of the application of the varying magnetic field and the initiation of the drop merging mechanism, the detectable signal being in the micro-Kelvin range and being at least five times greater than a signal resulting from the drop merging mechanism alone.

9. The device according to claim 8 wherein the magnetic material is in the form of a single magnetic bar.

10. The device according to claim 8 wherein the drop merging mechanism is based on electrostatic forces.

11. The device according to claim 8 wherein the drop merging mechanism is based on magnetic actuation.

12. The method according to claim 8 wherein the drops have a solid-liquid interface and one of a liquid-gas interface or a liquid-liquid interface.

* * * * *